US007385216B2

(12) United States Patent
Yoshigoe et al.

(10) Patent No.: US 7,385,216 B2
(45) Date of Patent: Jun. 10, 2008

(54) SENSOR DEVICE AND WIPER CONTROLLER HAVING SENSOR DEVICE

(75) Inventors: Taketoshi Yoshigoe, Kariya (JP); Junichi Ishikawa, Kariya (JP); Taiji Morishita, Kariya (JP)

(73) Assignee: Denso Corporation (JP)

( * ) Notice: Subject to any disclaimer, the term of this patent is extended or adjusted under 35 U.S.C. 154(b) by 0 days.

(21) Appl. No.: 11/239,121

(22) Filed: Sep. 30, 2005

(65) Prior Publication Data

US 2006/0076524 A1 Apr. 13, 2006

(30) Foreign Application Priority Data

Oct. 12, 2004 (JP) ............... 2004-297680

(51) Int. Cl.
*G01N 15/06* (2006.01)
*G02B 6/26* (2006.01)
*G05B 5/00* (2006.01)

(52) U.S. Cl. ................. 250/573; 250/227.25; 318/483

(58) Field of Classification Search ........ 250/573–575, 250/227.25; 356/445; 318/483; 73/170.17, 73/170.21; 340/602–604
See application file for complete search history.

(56) References Cited

U.S. PATENT DOCUMENTS

| 4,871,917 A | * | 10/1989 | O'Farrell et al. ......... 250/341.7 |
| 4,960,996 A | | 10/1990 | Hochstein .................. 250/349 |
| 5,498,866 A | | 3/1996 | Bendicks et al. ....... 250/227.25 |
| 5,661,303 A | | 8/1997 | Teder ....................... 250/341.8 |
| 5,831,730 A | * | 11/1998 | Traina et al. ............... 356/336 |
| 6,018,165 A | | 1/2000 | Kerkmann et al. ......... 250/574 |
| 6,285,037 B1 | * | 9/2001 | Koyama et al. ............ 250/574 |
| 6,433,501 B2 | | 8/2002 | Pientka ...................... 318/483 |
| 6,507,015 B1 | | 1/2003 | Maeno et al. .......... 250/227.25 |
| 6,686,992 B2 | | 2/2004 | Wakabayashi et al. ........ 356/72 |
| 6,744,371 B1 | | 6/2004 | Schmitt et al. ............. 340/602 |
| 6,768,099 B1 | | 7/2004 | Cheng et al. .......... 250/227.24 |

FOREIGN PATENT DOCUMENTS

| JP | 61-11637 | 1/1986 |
| WO | WO 95/27894 | 10/1995 |

OTHER PUBLICATIONS

European Search Report—Jan. 10, 2006.
Official Action dated Jun. 18, 2007 issued in copending U.S. Appl. No. 11/538,834.
Advisory Action dated Jan. 9, 2008 issued in U.S. Appl. No. 11/583,834.
Office Action dated Oct. 24, 2007 issued in Divisional U.S. Appl. No. 11/583,834.

* cited by examiner

*Primary Examiner*—Thanh X Luu
(74) *Attorney, Agent, or Firm*—Nixon & Vanderhye PC

(57) ABSTRACT

A sensor device for detecting wetting on a windshield includes a light emission element for emitting a light, a first light reception element for receiving the light in a first light path that includes reflective redirection by the windshield, and a second light reception element for receiving the light in a second light path that does not include reflective redirection by the windshield. The sensor device uses a ratio of the amount of the received light by the first light reception element and the amount of the received light by the second light reception element to determine wetting on the windshield.

11 Claims, 12 Drawing Sheets

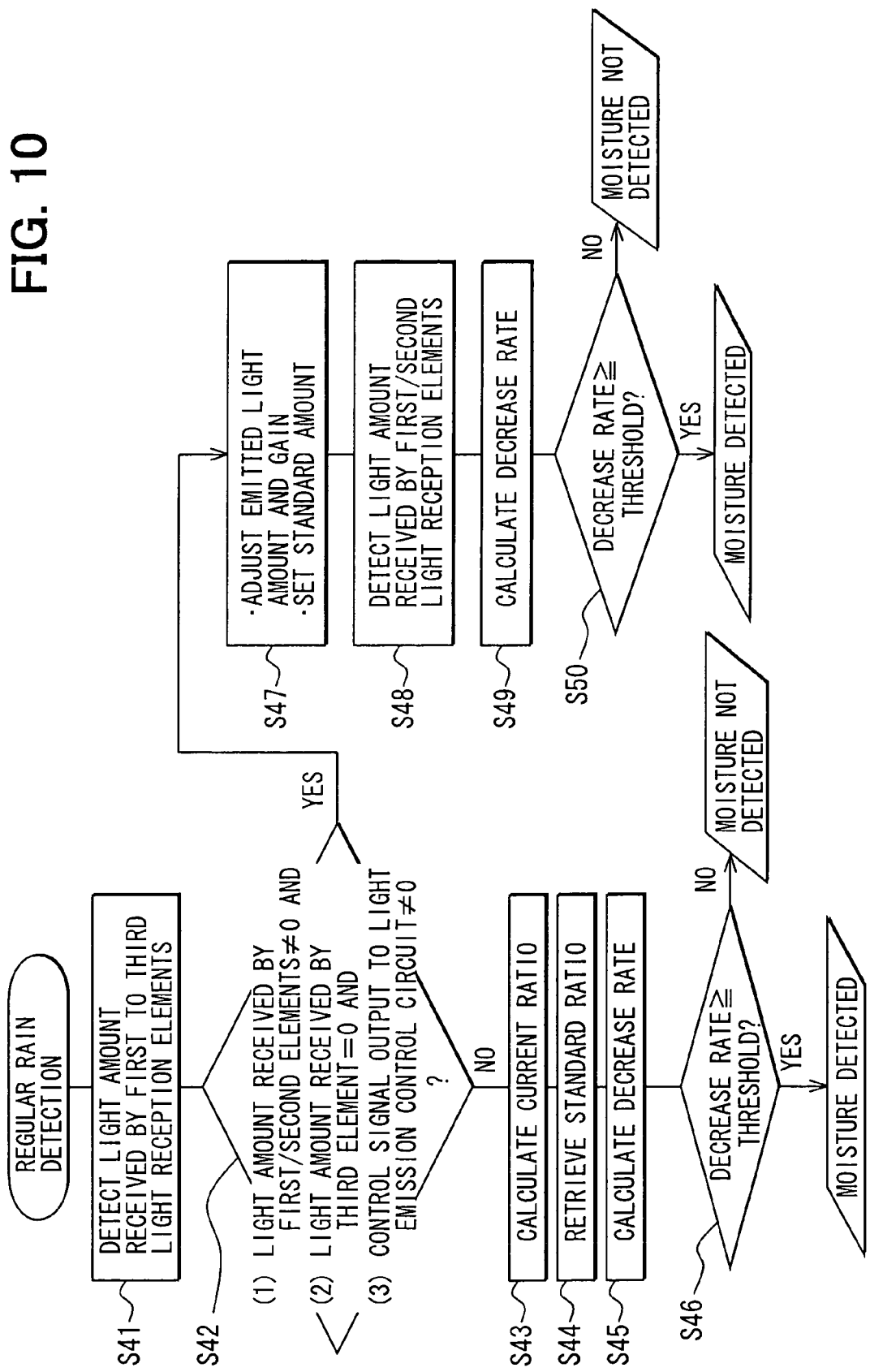

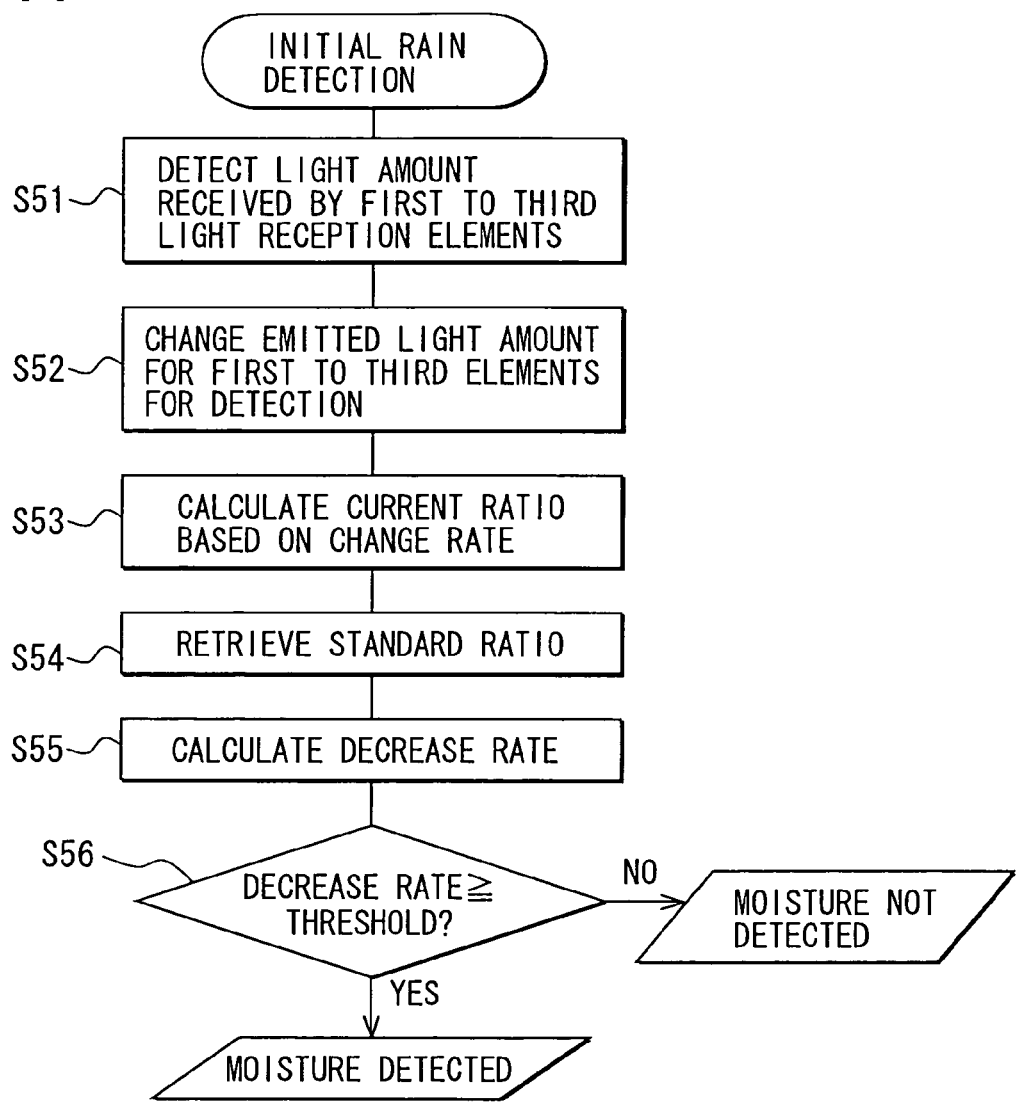

SENSOR DEVICE AND WIPER CONTROLLER HAVING SENSOR DEVICE

CROSS REFERENCE TO RELATED APPLICATION

This application is based on and claims the benefit of priority of Japanese Patent Application No. 2004-297680 filed on Oct. 12, 2004, the disclosure of which is incorporated herein by reference.

FIELD OF THE INVENTION

The present invention generally relates to a raindrop detection device and a wiper controller for controlling a wiping system of a windshield.

BACKGROUND OF THE INVENTION

A wiper controller conventionally uses a raindrop detection device for automatically controlling a wiping system that removes raindrops from a windshield of a vehicle.

The raindrop detection device uses a light emitted from a light emitting device and received by a light reception device for detecting moisture on the windshield. Japanese Patent Document JP-A-2001-349961 and U.S. Pat. No. 6,433,501 disclose the raindrop detection device that detects wet condition of the windshield due to moisture by measuring and detecting a difference of the amount of the light received by the light reception device. That is, the amount of the light received by the light reception device changes when a surface of the windshield is wet.

Characteristics of the light reception device used in the raindrop detection device changes depending on temperature of a surrounding environment. Therefore, it is important to know how to compensate the changed characteristics of the light reception device by taking the temperature into account. The Japanese Patent Document JP-A-2001-349961 discloses the temperature compensation of the characteristics based on a correlation of the characteristics and the temperature prepared and stored in the light reception device. In this manner, the raindrop detection device improves accuracy of detection of the moisture on the windshield.

Conventional raindrop detection devices have restrictions on the size of their casing because they are disposed on the windshield that is in a view of a driver of the vehicle. Therefore, a detection area of the raindrop detection device has to be maximized in terms of space utilization of projected size of the device. The United Patent Document U.S. Pat. No. 6,433,501 describes the arrangement of the light emitting devices and the light reception devices at the corners of a triangle/parallelogram in its disclosure. In this case, the light emitted from the light emitting device is received by the two light reception devices at the same time to effectively utilize a space in the raindrop detection device.

However, the raindrop detection device disclosed in the Japanese Patent Document JP-A-2001-349961 has to have correlation data over a broad range of temperature to compensate the temperature characteristics of the light reception device prior to the production of the device. The correlation data collection procedure by sampling outputs of the light reception device is not only time-consuming but leads to an increased cost of production. In addition, the data storage device for storing a large amount of the correlation data also contributes to the increase of the cost.

Further, the raindrop detection device disclosed in the U.S. Pat. No. 6,433,501 includes a space that can not be used for raindrop detection at the center of a triangle/parallelogram shape defined by the light emitting devices and the light reception devices at the corners of those figures. Therefore, the utilization of the space in the raindrop detection device in the disclosure is unavoidably restricted.

SUMMARY OF THE INVENTION

In view of the above-described and other problems, the present invention provides a raindrop detection device that has high accuracy in raindrop detection and high cost-performance. The present invention also provides a raindrop detection device that has a high space efficiency when it is disposed on a windshield of a vehicle.

According to an embodiment of the present invention, the raindrop detection device uses one light emitting device and two light reception devices for emitting and receiving a light. The two light reception devices receive the light from respectively different light paths. That is, a first light reception device and a second light reception device are used to receive the light, and the first light reception device receives the light reflected by the windshield, and the second light reception device receives the light that is not reflected by the windshield. In this manner, the first and the second light reception devices receive different amounts of the light emitted from the same light emitting device. Therefore, the ratio of the amounts of the light received by the two light reception devices is temperature independent, because the temperature dependent portion of the amounts of the light received by the light reception devices is cancelled in the course of calculating the ratio, that is, dividing one amount by the other amount both having the same temperature factors. As a result, the raindrop detection device that detects raindrops based on the change in the amount of the light reflected by the windshield is accurate regardless of the temperature of the environment. In addition, the ratio of the amounts of the received light by the first and the second light reception devices can be determined by using only one light emitting device, thereby reducing time and cost for collecting a large amount of data.

According to one aspect of the present invention, each of the two light reception devices receives the light at respectively different rate against the amount of the light originally emitted by the light emitting device. Therefore, each of the reception rates are temperature independent, because temperature dependent factors in the original amount of the light and in the received amount of the light cancel each other in the reception rate. As a result, the ratio of the two reception rates is also temperature independent, and the raindrop detection device can accurately detect raindrops by calculating the ratio of the reception rates derived from the two light reception devices. In addition, the ratio of the two reception rates of the received light by the first and the second light reception devices can be determined by measuring two amounts of the light emitted by the two light emitting devices, thereby reducing time and cost for data collection.

According to another aspect of the present invention, change in the amount of the light received by the light reception device can accurately be determined with a compensation of the temperature change taken into account. Therefore, the raindrop detection device can accurately detect raindrops on the windshield from the first detection operation after receiving a detection instruction.

According to yet another aspect of the present invention, the amount of data used for raindrop detection can be reduced by only storing either the ratio of the amounts of the received light from one light emitting device or the ratio of the reception rate of the light by the two light reception devices from two light emitting devices. Therefore, the capacity of data storage can be reduced to cost-effectively manufacture the raindrop detection device.

According to still another aspect of the present invention, the light emitted by the light emitting device is redirected by using a reflective surface in an optical device such as a prism or the like. Therefore, restriction on the position of the light reception device is reduced.

According to still yet another aspect of the present invention, the optical device conventionally used in the raindrop detection device includes the reflective surface for redirecting the light emitted by the light emitting device in the present embodiment. Therefore, the raindrop detection device can easily be assembled without compromising the secure emission of the light into the windshield from an inner surface of the windshield.

According to yet still another aspect of the present invention, the reflective surface is formed in a position between the windshield and a substrate being disposed substantially in parallel with the windshield for supporting the light emitting device and the light reception devices. Therefore, the raindrop detection device can have a small body.

According to yet still another aspect of the present invention, the light reception device collectively receives the light emitted by the light emitting device from a plurality of the light paths. That is, a first light path is reflectively redirected by the reflective surface and the windshield, while a second light path is reflectively redirected by a different portion of the windshield. In this manner, the raindrops on the windshield is effectively detected by the raindrop detection device. Therefore, the ratio of the detection area in a projection of the body of the raindrop detection device is increased. That is, the space in the raindrop detection device is effectively utilized.

According to yet still another aspect of the present invention, the light emitted by the light emitting device is received by two separate light receiving devices after reflectively redirected by the windshield. Therefore, the accuracy of the raindrop detection device is improved because of each of the amounts of the light received by the two separate light reception devices can be more accurately determined.

According to yet still another aspect of the present invention, the optical device has one or more reflective surfaces for redirecting the light emitted by the light emitting device. In addition, the reflective surfaces may be positioned between the windshield and the substrate for supporting the light emitting device and the light reception devices. Therefore, the raindrop detection device can be easily assembled without sacrificing the manufacturing cost and the projected size on the windshield.

Another embodiment of the present invention realized as a wiper controller uses the raindrop detection device described above for suitably controlling and actuating the wiping mechanism. The wiper controller incorporates the benefit of the embodiment of the raindrop detection device described above.

BRIEF DESCRIPTION OF THE DRAWINGS

Other objects, features and advantages of the present invention will become more apparent from the following detailed description made with reference to the accompanying drawings, in which:

FIG. 10 shows a flowchart of wiper control process in a regular raindrop detection step in a third embodiment;

FIG. 11 shows a flowchart of wiper control process in an initial raindrop detection step in a fourth embodiment;

DETAILED DESCRIPTION OF THE PREFERRED EMBODIMENTS

A raindrop detection device of the present invention is described with reference to the drawings.

First Embodiment

Figure 2:
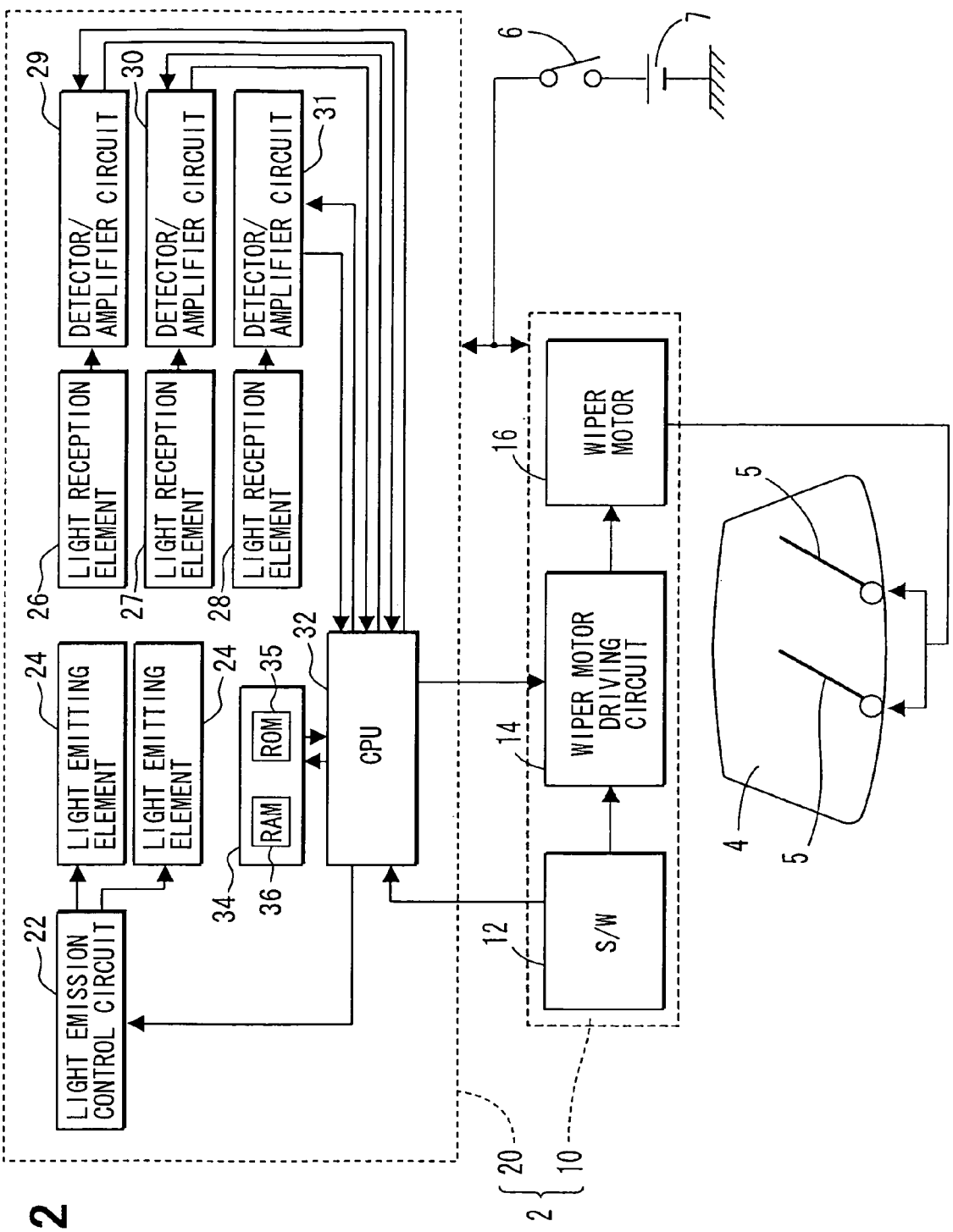
FIG. 2 shows a block diagram of a wiper controller in the first embodiment.

FIG. 2 shows a block diagram of a wiper controller in the first embodiment of the present invention. The wiper controller 2 controls wipers 5 used in a vehicle for wiping raindrops on a windshield 4.

The wiper controller 2 includes a wiper driving device 10 and a raindrop detection device 20. Electric power supply is provided from a battery 7 to the wiper driving device 10 and the raindrop detection device 20 through an ignition switch 6.

The wiper driving device 10 includes a wiper switch 12, a wiper motor driving circuit 14, and a wiper motor 16. The wiper switch 12 is disposed at a position that is close to a driver's seat in the vehicle. The wiper switch 12 has a plurality of control positions of wiping operation such as "auto," "low," "middle," "high," "stop" and the like. The wiper switch 12 outputs a control position signal that indicates a control position of the switch 12 to the wiper motor driving circuit 14 and a CPU 32 in the raindrop detection device 20. The wiper motor driving circuit 14 controls the operation of the wiper motor 16 based on the signals from the wiper switch 12 and the CPU 32 in the raindrop detection device 20. More practically, the wiper motor driving circuit 14 drives the wiper motor 16 based on a signal from the CPU 32 when the control position signal from the wiper switch 12 indicates that the control position of the switch 12 is in the "auto" position. The wiper motor driving circuit 14 drives the wiper motor 16 in a speed according to the control position signal when the control position signal from the wiper switch 12 indicates that the switch 12 is either in the "low," "middle," or "high" position. The wiper motor driving circuit 14 stops the operation of the wiper motor 16 when the control position signal from the wiper switch 12 indicates that the switch 12 is in the "stop" position. The wiper motor 16 drives the wipers 5 in a rocking motion based on a signal from the wiper motor driving circuit 14, and holds the wipers 5 at a position that is close to a hood of the vehicle when the wiper motor driving circuit 14 stops the operation of the wiper motor 16.

Figure 1:
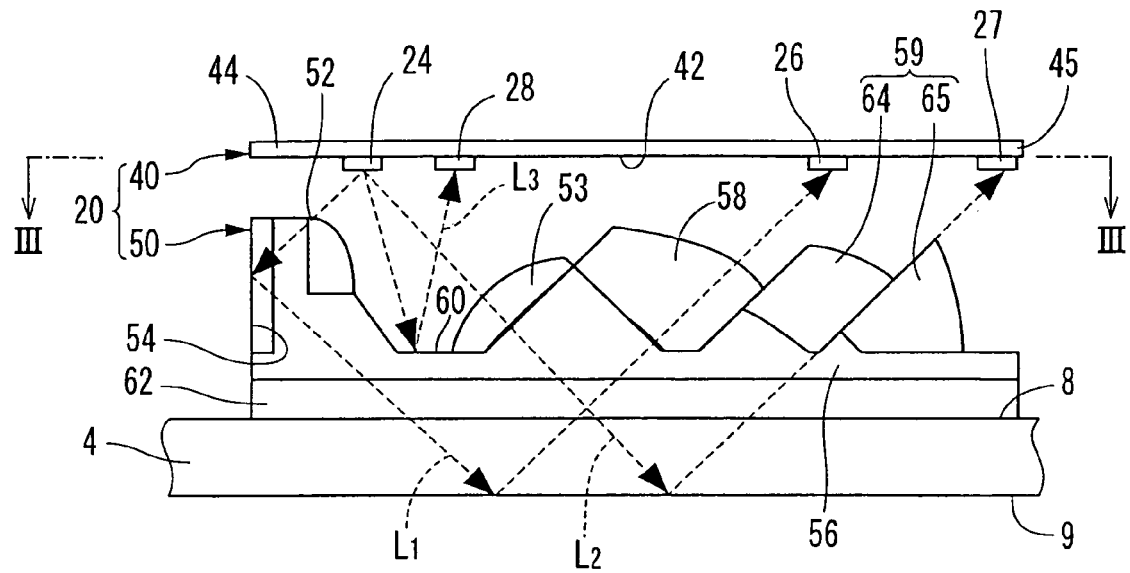
FIG. 1 shows a side view of a raindrop detection system in a first embodiment of the present invention.

The raindrop detection device 20 is disposed on an inner surface 8 of the windshield 4, and detects raindrops, moisture, or the like on an outer surface 9 of the windshield 4 shown in FIG. 1. A projection of the raindrop detection device 20 on the windshield 4 falls within a sweep area of the wiper 5.

The raindrop detection device 20 includes a light emission control circuit 22, a light emitting element 24, a first, second and third light reception elements 26, 27, 28, a detector/amplifier circuit 29, 30, 31, a CPU 32, and a memory 34.

The light emission control circuit 22 controls an electric current supplied to the light emitting element 24 based on a control signal from the CPU 32.

A light emitting diode in the light emitting element 24 emits a light such as an infrared light by taking the electric current supplied from the light emission control circuit 22.

Photo diodes in the first, second and third light reception elements 26, 27, 28 receive the light from respectively different light paths. The three light reception elements 26, 27, 28 are connected to corresponding detector/amplifier circuits 29, 30, 31, and output detection signals to the detector/amplifier circuits 29, 30, 31 indicative of the amounts R1, R2, R3 of received light by the light reception elements.

The three detector/amplifier circuits 29, 30, 31 linearly amplify the detection signals from the corresponding light reception elements for outputting them to the CPU 32. The signal amplification process takes place substantially in synchronization with the reception process of the detection signals. Further, gain of the detector/amplifier circuits 29, 30, 31 are controlled by other control signals from the CPU 32.

The CPU 32 executes a control program stored in the ROM 35 of the memory 34 for generating the control signals to be sent to the wiper motor driving circuit 14, the light emission control circuit 22, and the detector/amplifier circuit 29, 30, 31. The RAM 36 in the memory 34 temporarily stores calculation data used in the CPU 32 for calculation.

Figure 3:
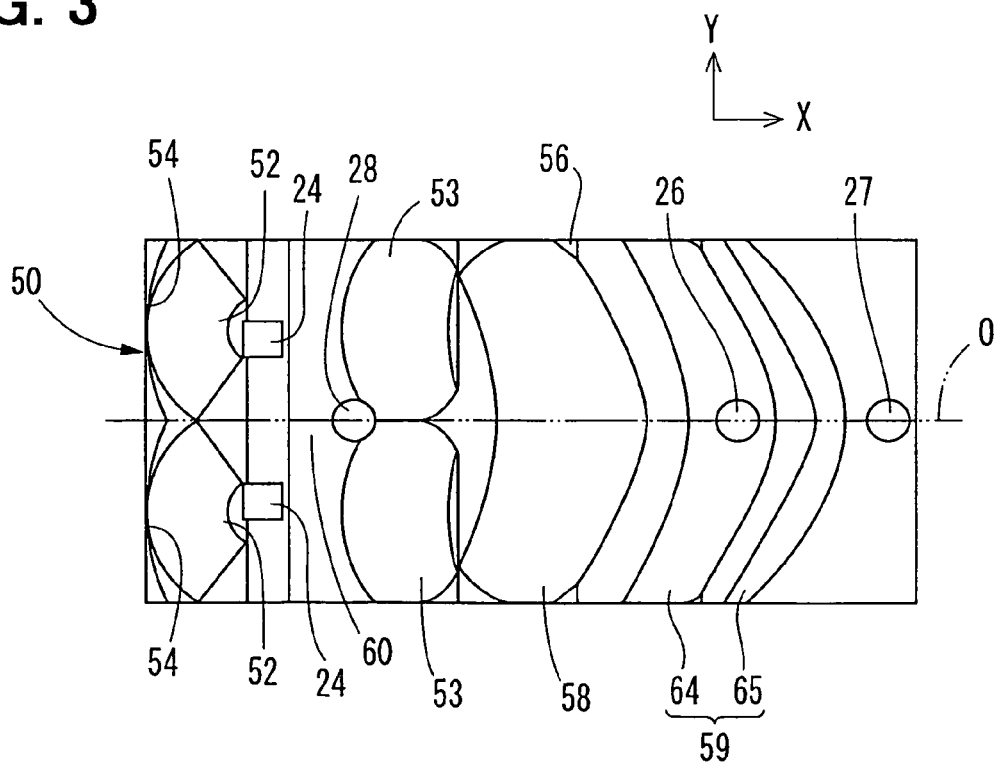
FIG. 3 shows a cross sectional view of the raindrop detection system along III-III line in FIG. 1.

The raindrop detection device 20 shown in FIGS. 1 and 3 further includes a substrate 40 and an optical device 50. In the following description, a horizontal direction in FIG. 3 is defined as X direction, and a vertical direction in FIG. 3 is defined as Y direction.

The substrate 40 is fixed on the inner surface 8 of the windshield 4 with a member interposed therebetween (not shown in the figure). The substrate 40 is substantially in a shape of flat panel, and has a panel surface 42 that is substantially in parallel with the inner surface 8 of the windshield 4. The substrate 40 has the light emitting element 24, and the first to third light reception elements 26 to 28 on the panel surface 42. The two light emitting elements 24 are disposed on the panel surface 42 symmetrically on both sides of a virtual plane O (ou) that intersects and divides the panel surface 42 of the substrate 40 into two equal parts in Y direction in FIG. 3. The light reception elements 26 to 28 are also positioned on the virtual plane O. The light emitting element 24, the third light reception element 28, the first light reception element 26 and the second light reception element 27 are positioned in this order on the virtual plane O when X direction is defined as a direction from a first end 44 of the substrate 40 to a second end 45.

The optical device 50 is made of resin, and includes a first and second collimator lens 52, 53, a first reflector 54, a prism 56, a first and second convergence lens 58, 59, and a reflective surface 60. The prism 56 is fixed on the inner surface 8 of the windshield 4 with a transparent silicon sheet 62 interposed therebetween. The optical device 50 has these elements 52 to 54 and 58 to 60 disposed on an opposite side of the prism 56 relative to the inner surface 8. In this manner, a whole part of the optical device 50 is disposed between the substrate 40 and the windshield 4.

The first collimator lens 52 is disposed on both sides of the virtual plane O, and the first reflector 54 is disposed in the same manner on both sides of the virtual plane O. The first collimator lens 52 is a plane-convex lens with its optical axis transpiercing the light emitting element 24 and the first reflector 54 on the same side of the virtual plane O. That is, the light from the light emitting element 24 is redirected through the first collimator lens 52 toward the first reflector 54. The first collimator lens 52 is positioned on the first end 44 side of the substrate 40 relative to the light emitting element 24 in X direction, and the optical axis of the first collimator lens 52 substantially has an angle of 45 degrees against the outer surface 9 of the windshield 4. The first reflector 54 is substantially perpendicular to the outer surface 9 of the windshield 4 and to the panel surface 42 of the substrate 40. The first reflector 54 is positioned on the first end 44 side relative to the light emitting element 24 and the first collimator lens 52 in X direction. The first reflector 54 is used to redirect the light from the first collimator lens 52 toward the prism 56.

The second collimator lens 53 is disposed on both sides of the virtual plane O. The second collimator lens 53 is a plane-convex lens with its optical axis transpiercing the light emitting element 24 on the same side of the virtual plane O. That is, the light from the light emitting element 24 is redirected through the second collimator lens 53 toward the prism 56. The optical axis of the second collimator lens 53 substantially has an angle of 45 degrees against the outer surface 9 of the windshield 4, and, at the same time, substantially has an angle of 90 degrees against the optical axis of the first collimator lens 52. The second collimator lens 53 is positioned on the second end 45 side of the substrate 40 relative to the light emitting element 24 in X direction.

The prism 56 redirects both of the light in the first light path L1 via the first collimator lens 52 and the first reflector 54 and the light in the second light path L2 via the second collimator lens 53 into the windshield 4 from the inner surface 8 side toward the outer surface 9 of the windshield 4. Then, the light is redirected by the outer surface of the windshield 4.

Figure 4:
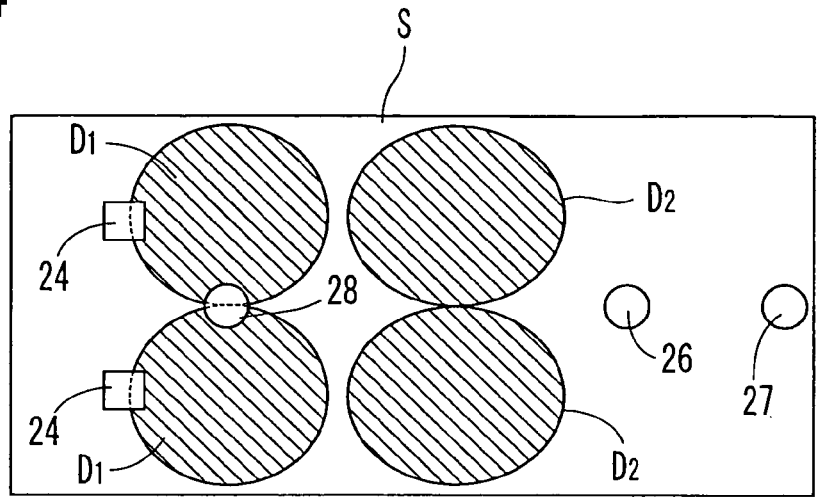
FIG. 4 shows an illustration of detection areas of the raindrop detection system in the first embodiment.

The first convergence lens 58 extends from one side of the substrate 40 to the other side in Y direction, that is, both sides of the virtual plane O is covered by the single first convergence lens 58. The first convergence lens 58 is a plane-convex lens with its optical axis transpiercing the first light reception element 26. The first convergence lens 58 is positioned on the second end 45 side of the substrate 40 relative to the light emitting element 24 and the second collimator lens 53 in X direction. The optical axis of the first convergence lens 58 substantially has an angle of 45 degrees against the outer surface 9 of the windshield 4. The first convergence lens 58 receives the light in the first light path L1 being redirected by the outer surface 9 of the windshield 4 through the prism 56. Then, the first convergence lens 58 redirects the light toward the first light reception element 26. An oval area D1 shown in an illustration in FIG. 4 is a detection area on the outer surface 9 on the windshield 4. The light redirected in this area D1 can be received by the first light reception element 26. The amount R1 of the light received by the first light reception element 26 decreases when the area D1 is covered by moisture, e.g., raindrops. That is, in FIG. 4, the area D1 is the area that is used for raindrop detection in a rectangular projection area S onto the windshield 4 of a body of the raindrop detection device 20.

The second convergence lens 59, as shown in FIGS. 1 and 3, extends from one side of the substrate 40 to the other side in Y direction, that is, both sides of the virtual plane O is covered by the single second convergence lens 59. The second convergence lens 59 is a combination of two plane-convex lenses 64, 65 in line in X direction with its optical axis transpiercing the second light reception element 27. The second convergence lens 59 is positioned on the second end 45 side of the substrate 40 relative to the light emitting element 24 and the first convergence lens 58 in X direction. The optical axis of the plane-convex lens 64, 65 in the second convergence lens 59 substantially has an angle of 45 degrees against the outer surface 9 of the windshield 4. The second convergence lens 59 receives the light in the second light path L2 being redirected by the outer surface 9 of the windshield 4 through the prism 56. Then, the second convergence lens 59 redirects the light toward the second light reception element 27. An oval area D2 shown in an illustration in FIG. 4 is a detection area on the outer surface 9 on the windshield 4. The area D2 is positioned outside of the detection area D1 in this embodiment. The light redirected in this area D2 can be received by the second light reception element 27. The amount R2 of the light received by the second light reception element 27 decreases when the area D2 is covered by moisture, e.g., raindrops. That is, in FIG. 4, the area D2 is the area that is used for raindrop detection on the windshield 4.

The reflective surface 60, as shown in FIGS. 1 and 3, extends from one side of the substrate 40 to the other side in Y direction. The reflective surface 60 is positioned substantially in parallel with the outer surface 9 of the windshield 4 and the panel surface 42 of the substrate 40. The reflective surface 60 is positioned between the light emitting element 24 and the third light reception element 28 beside being positioned between the first collimator lens 52 and the second collimator lens 53. The reflective surface 60 redirects the light from the light emitting element 24 toward the third light reception element 28. Therefore, the light is redirected in a third light path L3 from the light emitting element 24 to the light reception element 28 through the reflective surface 60 without going through the windshield 4.

Figure 5:
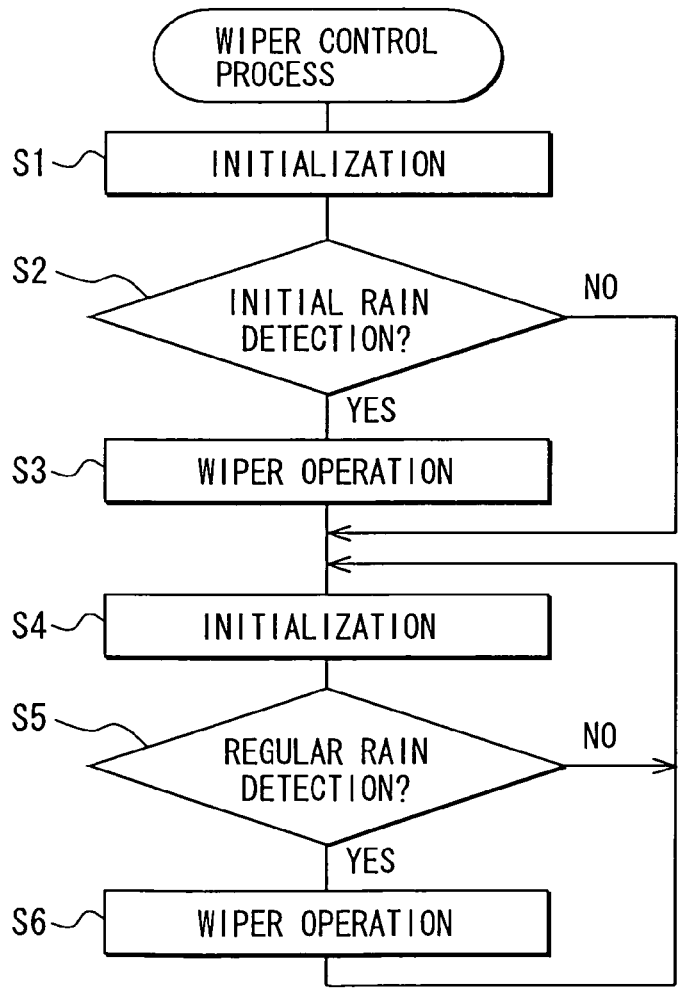
FIG. 5 shows a flowchart of wiper control process in an auto mode in the first embodiment.

An automatic wiper control process is described with reference to a flowchart in FIG. 5. The automatic wiper control process starts when the ignition switch 6 is turned to ON and the position of the wiper switch 12 is in the "auto" position, and the automatic wiper control process ends when the ignition switch is turned to OFF, or when the wiper switch 12 is put in a position other than the "auto" position.

In step S1, the process initializes the RAM 36. In step S2, an initial rain detection is executed for initially detecting moisture on the windshield 4. The process proceeds to step S3 for driving the wiper 6 once by outputting the control signal to the wiper motor driving circuit 14 when moisture is detected before proceeding to step S4. The process directly proceeds to step S4 when moisture is not detected.

In step S4, the RAM 36 is initialized. In step S5, a regular rain detection is executed for regularly detecting moisture on the windshield 4. The control signal for driving the wiper 6 for a predetermined cycle in a certain speed is output to the wiper motor driving circuit 14 in step 6 when moisture is detected before returning to step S4. The process directly returns to step S4 when no moisture is detected.

Figure 6:
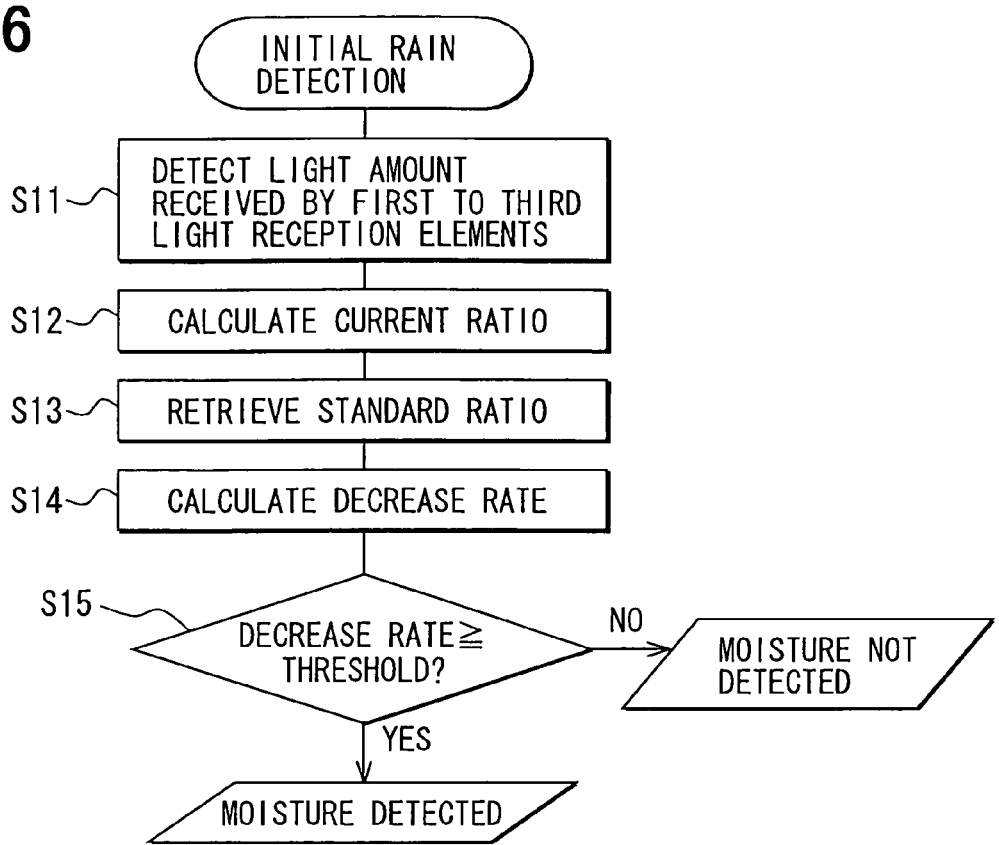
FIG. 6 shows a flowchart of wiper control process in an initial rain detection step in FIG. 5 in the first embodiment.

The initial rain detection and the regular rain detection are described in detail in the following. The process of the initial rain detection is described with reference to the flowchart in FIG. 6.

In step S11, each of the light emitting elements 24 is used to emit the light in order, and the amounts R1, R2, R3 of the light received by the first, second and third light reception elements are detected. The light emission control circuit 22 and each of the detector/amplifier circuits are respectively controlled by the control signals in terms of the total emission amount of the light and the gain of the detection signals.

Figure 7A:
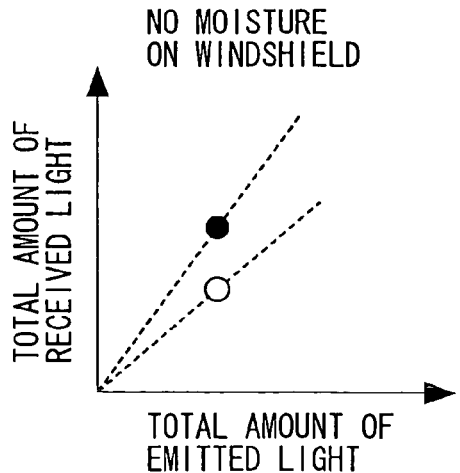
FIG. 7A shows a diagram of relationship between a total amount of emitted light and a total amount of received light on a dry windshield in the initial rain detection step in the first embodiment.
Figure 7B:
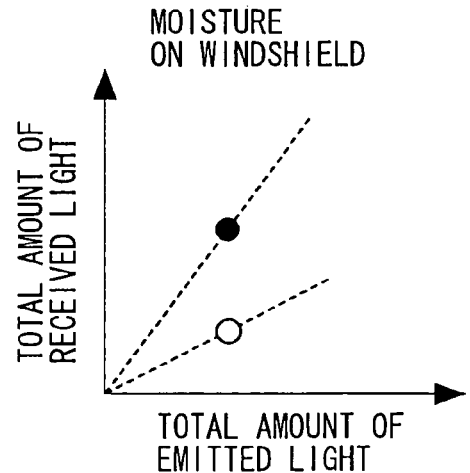
FIG. 7B shows a diagram of relationship between a total amount of emitted light and a total amount of received light on a wet windshield in the initial rain detection step in the first embodiment.

The detection signals are interpreted as the amounts of the received light R1, R2, R3. Then, the amounts of the received light R1, R2, R3 by the light reception elements are stored in the RAM 36. Broken lines having a white circle in diagrams in FIGS. 7A and 7B show relationships between a total amount of emitted light from the light emitting elements 24 and a total amount of received light by the first and second light reception elements 26, 27 (R1+R2). These amount are calculated in step S11. The diagrams show that the amount of received light decreases when the windshield 4 has moisture on it. This is because the areas D1 and D2 reflect a smaller amount of light when the windshield 4 is wet.

Broken lines having a black circle in diagrams in FIGS. 7A and 7B show relationships between an amount of emitted light from the light emitting elements 24 and a total amount of received light by the third light reception element 28 (R3).

These amount are calculated in step S11. The diagrams in FIGS. 7A and 7B show that the amount of received light does not substantially change when the windshield 4 has moisture on it. This is because the light received by the third light reception element 28 takes an light path that is not reflected by the windshield 4.

A ratio of the total amount of the received light R1+R2 against the amount of the received light R3 can be used as an index of moisture on the windshield 4, because temperature characteristic of the light reception elements are the same for all three elements. That is, by taking the ratio of the two received light amounts, the temperature fluctuation factor is removed from calculation without causing change in moisture related factor.

In step S12, the amounts R1, R2, R3 are retrieved from the RAM 36, and a current ratio Cr=R3/(R1+R2) is calculated. In step S13, a standard ratio Cm calculated by using the same equation in a factory as a standard value for a dry condition is retrieved from the ROM 35.

In step 14, the current ratio Cr is divided by the standard ratio Cm. This rate of two ratios is calculated as a decrease rate F. The decrease rate F is greater than 1 when the windshield 4 is wet.

In step 15, the decrease rate F is compared with a threshold Fth. The windshield 4 is determined as wet when the decrease rate F is equal to or greater than the threshold Fth. The windshield 4 is determined as dry when the decrease rate F is smaller than the threshold Fth. The threshold Fth is defined as a certain value that is greater than 1 in consideration of an error caused by external disturbance or the like.

Figure 8:
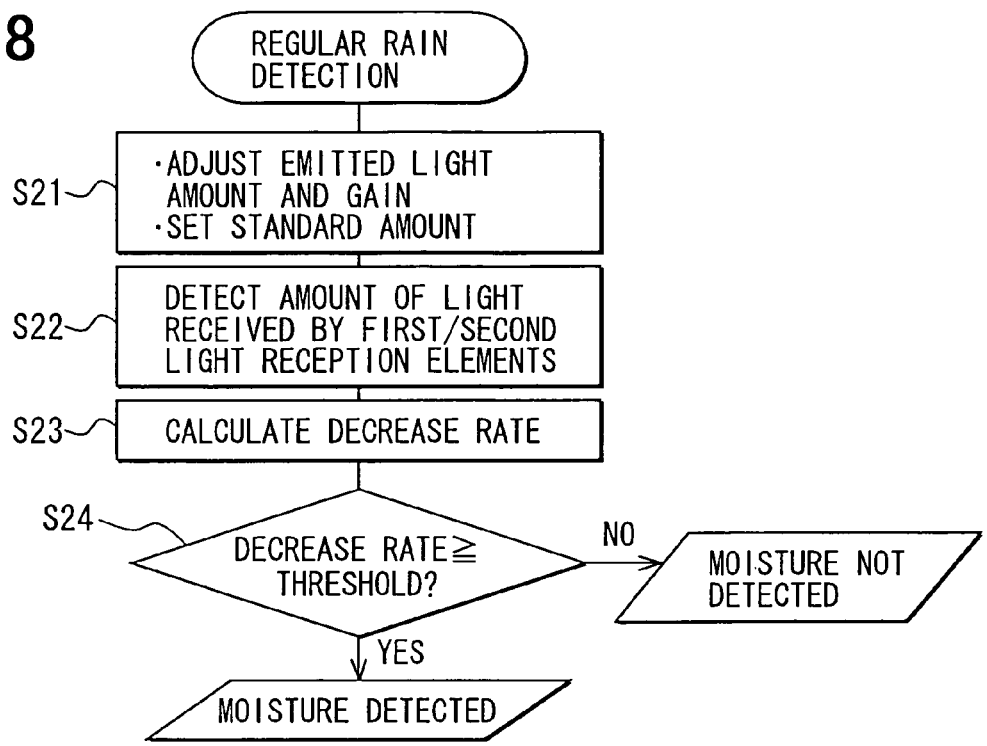
FIG. 8 shows a flowchart of wiper control process in a regular rain detection step in the first embodiment.

FIG. 8 shows a flowchart of a process for the regular rain detection.

In step S21, the total amount of emitted light from the light emitting elements 24 and the gain of the detector/amplifier circuit 29, 30 are adjusted based on an operation of the light emission control circuit 22 and the detector/amplifier circuit 29, 30 at an occasion when no moisture exists on the windshield 4, that is, for example, when the wiper 5 swept the detection area of the raindrop detection device 20. In the present embodiment, step S21 is executed after the initial rain detection in step S2 gives a negative result (NO branch), or after a sweep of the wiper 5 in step S3 or step S6. In this step, the amounts of received light R1 and R2 can be regarded as the amounts for a dry condition. Therefore, the amounts R1 and R2 detected in this step are stored as standard amount-s Rb1 and Rb2 for raindrop detection.

In step S22, each the light emitting elements 24 are lit at a predetermined interval for measuring the amount of light R1 and R2 received by the first and second light reception element 26, 27. The total amount of emitted light and the gain of the detector/amplifier circuits 29, 30 are controlled to be the values that are defined in step S21. The amounts of light received by the light reception element 26, 27 in this step are stored in the RAM 36.

In step S23, the ratio of the amount R1+R2 against the amount Rb1+Rb2 is calculated as the decrease rate F. In this step, the decrease rate F is calculated as a percentage. The decrease rate F is greater than 0% when the windshield 4 is wet.

In step S24, the decrease rate F is compared with the threshold Fth. The windshield 4 is determined as wet when the decrease rate F is equal to or greater than Fth. The windshield 4 is determined as dry when the decrease rate F is smaller than Fth. The threshold Fth is defined as a certain value that is greater than 0 in consideration of an error caused by external disturbance or the like.

It is advantageous that the initial rain detection in the wiper control process in the present embodiment accurately detect moisture on the windshield 4 because the temperature factor is removed by taking a ratio of two amounts of the light from respectively separate light paths. That is, moisture on the windshield 4 can be accurately detected immediately after the wiper switch 12 is put in the "auto" position. Further, the standard ratio used as criteria can be determined by measuring only one set of values of R1, R2, R3. In this manner, time for the measurement and cost for data storage are reduced. Furthermore, the detection of moisture is more efficiently processed because the regular rain detection is processed by a fewer number of steps than the initial rain detection.

It is also advantageous that the projection of the raindrop detection device 20 on the windshield 4 is efficiently used for detecting moisture because the detection areas D1 and D2 do not overlap. That is, the projection of the device 20 includes very little space that is not used for detecting moisture. Further, the amount of light is accurately detected by using separate light reception element for each the respective light paths from the detection areas D1 and D2.

It is also advantageous that the optical device 50 integrally includes the prism 56, the first reflector 54 and the reflective surface 60 beside having the lenses 52, 53, 58, 59 in one body. In this manner, the process of assembly of the raindrop detection device 20 is simplified.

It is also advantageous that the body of the raindrop detection device 20 has compactness by arranging the optical device 50 between the substrate 40 and the windshield 4. In this manner, a driver of the vehicle can have an increased area of view through the windshield 4.

Second Embodiment

Figure 9:
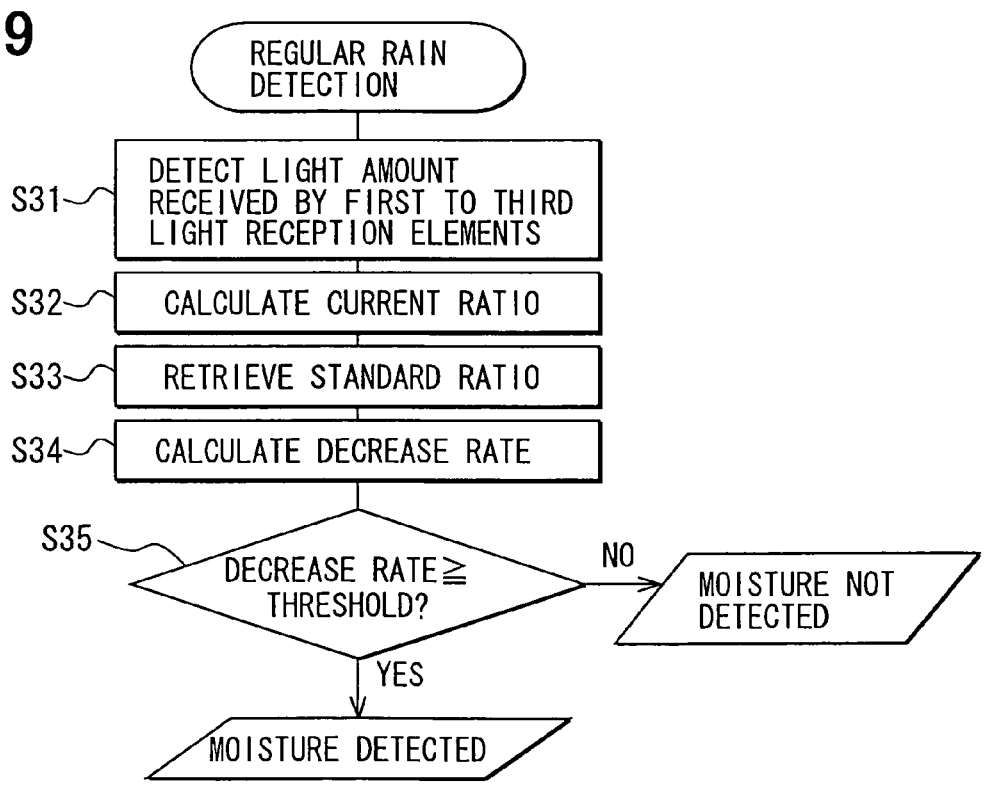
FIG. 9 shows a flowchart of wiper control process in a regular raindrop detection step in a second embodiment.

In the present embodiment, the wiper controller processes the regular rain detection in the same way as the initial rain detection as described in the first embodiment. That is, steps S31 to S35 in the flowchart in FIG. 9 are the same as steps S11 to S15 in the flowchart in FIG. 6 in the first embodiment. In this manner, the control process of the wiper controller is simplified without compromising the accuracy of detection.

Third Embodiment

The regular rain detection of the wiper control process in a third embodiment of the present invention is described with reference to a flowchart in FIG. 10.

The regular rain detection starts with step S41, which is the same process as step S11 in the initial rain detection.

In step S42, three fail-safe criteria are examined. That is, the process proceeds to step S43 if at least one of the three criteria is met. In this case, the process is determined as a normal condition. The process proceeds to step S47 if all of the three criteria are met. The process proceeds to step S47 for handling an abnormal condition based on the examination of the three criteria.

The three criteria for fail-safe are as follows:

(1) Each of the amounts R1, R2 of the light received by the first and second light reception elements stored in the RAM 36 in step S41 is not 0;

(2) The amount R3 of the light received by the third light reception element is 0; and (3) The control signal to the light emission control circuit 22 is not 0.

In steps S43 to S46, the process is the same as the initial rain detection in steps S12 to S15. In steps S47 to S50, the process is the same as the regular rain detection in steps S21 to S24 in the first embodiment.

In the normal condition based on the above criteria, the wiper 5 is controlled accurately according to the ratio of R3/(R1+R2) while the wiper switch 12 is put in the "auto" position. In the abnormal condition based on the above criteria, the wiper control is executed based on the process for the regular rain detection. In this manner, a situation where the "auto" position of the wiper switch 12 does not work properly is avoided.

Fourth Embodiment

The process of the initial rain detection in a fourth embodiment of the present invention is described with reference to a flowchart in FIG. 11.

In step S51, the process of the initial rain detection starts with uses each of the light emitting elements 24 in order to emit the light to the first, second, and third light reception elements 26 to 28 for detecting the amounts of light from the light emitting elements 24. The light emission control circuit 22 controls the total amount of light emitted from the light emitting elements 24 to be a value T1 based on a received signal, and the gains of the detector/amplifier circuits 29 to 31 are respectively controlled to be values A1, A2, A3 based on other received signals. In this manner, the amounts of light received by the light reception elements 26 to 28 are stored in the RAM 36 as the values R1, R2, R3.

In step S52, each of the light emitting elements 24 are used to emit different amounts of light to the light reception elements 26 to 28. The light emission control circuit 22 controls the total amount of light emitted from the light emitting elements 24 to be a value T2 based on a received signal, and the gains of the detector/amplifier circuits 29 to 31 are respectively controlled to be the same values A1, A2, A3 based on other received signals. In this manner, the amounts of light received by the light reception elements 26 to 28 are stored in the RAM 36 as the values R1, R2, R3.

Figure 12A:
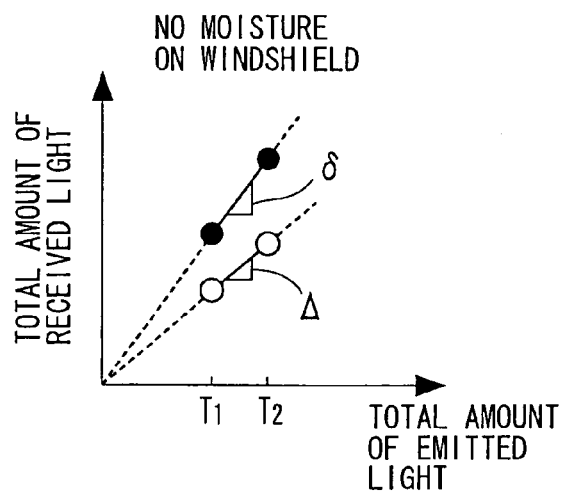
FIG. 12A a diagram of relationship between a total amount of emitted light and a total amount of received light on a dry windshield in the initial rain detection step in the fourth embodiment.
Figure 12B:
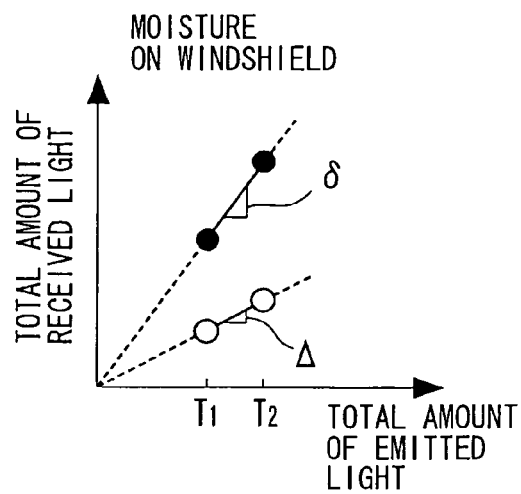
FIG. 12B shows a diagram of relationship between a total amount of emitted light and a total amount of received light on a wet windshield in the initial rain detection step in the fourth embodiment.

FIGS. 12A and 12B Show Relationships

Broken lines having a white circle in diagrams in FIGS. 12A and 12B show relationships between a total amount of emitted light from the light emitting elements 24 and the total amount of received light by the first and second light reception elements 26, 27 (R1+R2). A symbol "Δ" in FIGS. 12A and 12B represents a ratio of two differences, that is, the difference between two total amounts of received light R1+R2 in steps S51 and 52, and the difference between the amounts of emitted light T1 and T2. This ratio represents a change rate of the total amount of received light R1+R2 against a unit amount of emitted light. The change rate Δ decreases when the windshield 4 has moisture on it. The decrease of the change rate Δ is shown in FIGS. 12A and 12B. This is because the areas D1 and D2 on the windshield 4 reflect a smaller amount of light when the windshield 4 is wet.

Broken lines having a black circle in diagrams in FIGS. 12A and 12B show a relationship between an amount of emitted light from the light emitting elements 24 and an amount of received light by the third light reception element 28 (R3). A symbol "δ" in FIGS. 12A and 12B represents a ratio of two differences, that is, the difference between two amounts of received light R3 in steps S51 and 52, and the difference between the amounts of emitted light T1 and T2. The diagrams in FIGS. 12A and 12B show that the amount of received light does not substantially change when the windshield 4 has moisture on it. This is because the light received by the third light reception element 28 takes an light path that is not reflected by the windshield 4. This ratio represents a change rate of the amount of received light R3 against a unit amount of emitted light. The change rate δ is the same for both of the wet condition and dry condition of the windshield 4. The decrease of the change rate Δ is shown in FIGS. 12A and 12B. This is because the light from the light emitting element 24 does not go through the windshield 4.

The change rate Δ by itself can be used as an index of raindrop detection. However, the change rate Δ fluctuates when temperature around the raindrop detection device 20 changes. The temperature dependent factor in the change rate Δ can be cancelled by taking the ratio of the change rate Δ against the change rate δ because temperature characteristics of the light reception elements 26, 27 and the light emitting elements 24 are substantially the same. The change rate 8 is suitable as a denominator because it is not dependent on the condition of the windshield 4.

In step S53, the change rate A and the change rate δ are calculated based on the detected amounts of the received light R1, R2, R3 stored in the RAM 36. Then the current ratio Cr=δ/Δ is calculated. The standard ratio Cm calculated as a representative value of the dry condition of the windshield 4 is retrieved from the ROM 35 in step S54.

In steps S55 and S56, the process is same as steps S14 and S15 described in the first embodiment for finishing the initial rain detection.

Therefore, the process for the initial rain detection can accurately detect moisture on the windshield 4 by calculating the change rates Δ and δ because of the removal of the temperature factor from the output signal immediately after a start of the wiper operation when the wiper switch 12 is put in the "auto" position. The ratio can be calculated by measuring the amount of light only at two points. Therefore, the time for the measurement and the cost for storing the measured data are decreased.

Further, the initial rain detection in the fourth embodiment may be used as the regular rain detection in the first embodiment, the regular rain detection in the second embodiment, and the initial and regular rain detection in the third embodiment.

Fifth Embodiment

A fifth embodiment of the present invention is described with reference to the drawings.

Figure 13:
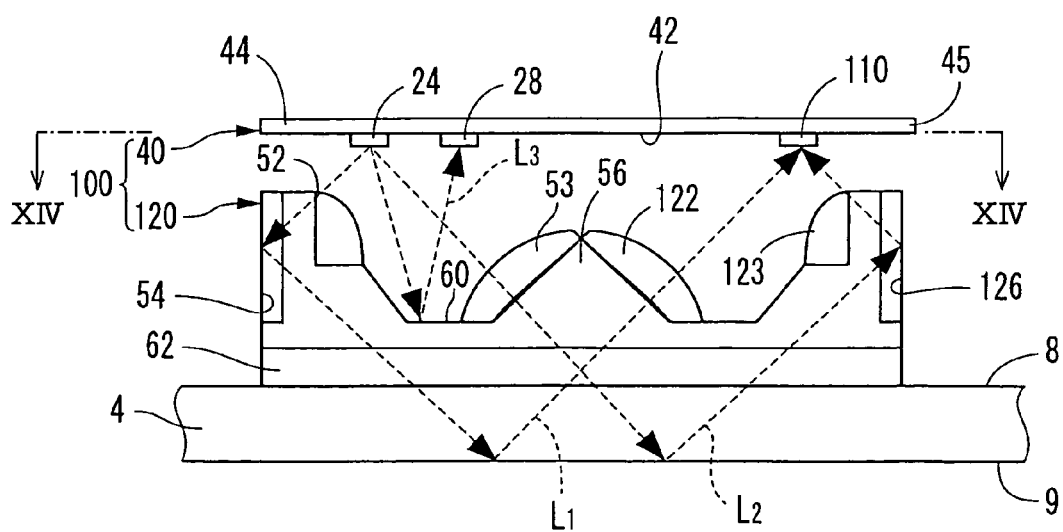
FIG. 13 shows a side view of the raindrop detection system in a fifth embodiment.
Figure 14:
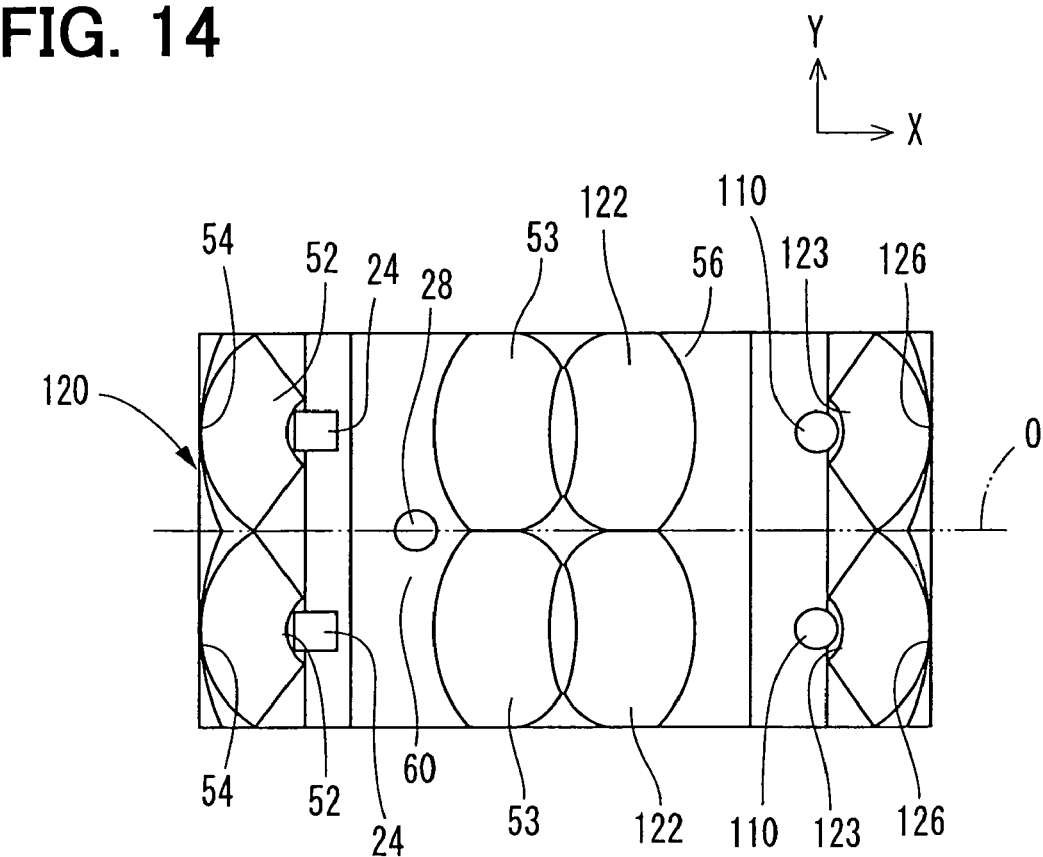
FIG. 14 a cross sectional view of the raindrop detection system along XIV-XIV line of the raindrop detection system in FIG. 13.

FIGS. 13 and 14 show a side view and a top view of the raindrop detection device 100. More specifically, FIG. 14 shows a top view of the raindrop detection device 100 taken from the windshield 4 side surface of the substrate 40.

Figure 15:
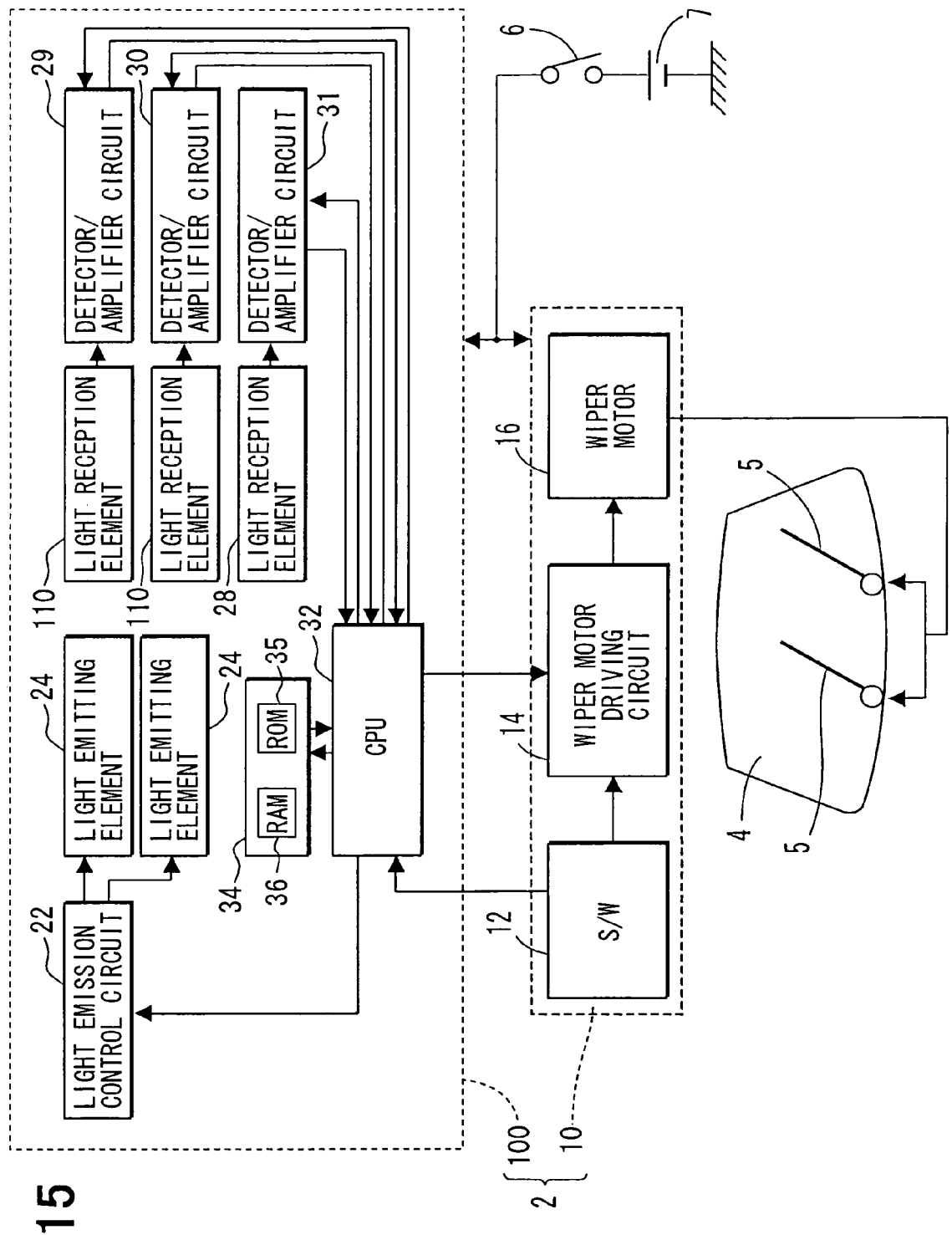
FIG. 15 shows a block diagram of a wiper controller in the fifth embodiment.

The raindrop detection device 100 includes a substrate 40, and the panel surface 42 of the substrate 40 has two light reception elements 110 respectively disposed on both sides of the virtual plane O. In the present embodiment, the two light reception elements 110 is designated as the first light reception elements 110, and the light reception element 28 is designated as the second light reception element 28. The substrate 40 has the first collimator lens 52, the light emitting element 24s, the second light reception element 28, the second light collimator lens 53, and the first light reception elements 110 disposed thereon in order of X direction from the first end 44 to the second end 45. One of the two first light reception elements 110 is connected to the detector/amplifier circuit 29, and the other first light reception element 110 is connected to the detector/amplifier circuit 30 as shown in FIG. 15.

The optical device 120 in the raindrop detection device 100 of the present embodiment is different in shape from the optical device 50 in the first embodiment. That is, the first and second convergence lenses 122, 123 included in the optical device 120 are different from the convergence lenses 58, 59 used in the first embodiment. The optical device 120 also includes a second reflector 126 in addition to the first reflector 54.

Figure 16:
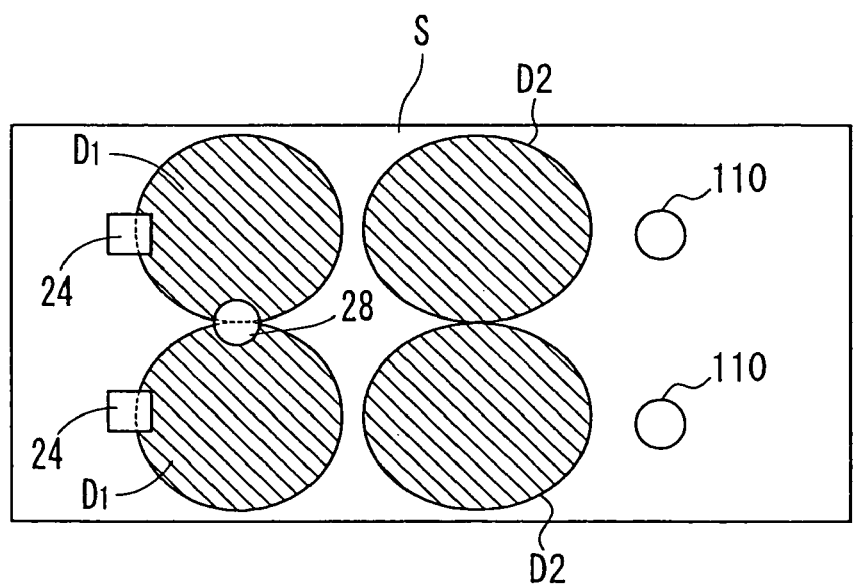
FIG. 16 shows an illustration of detection areas of the raindrop detection system in the fifth embodiment.

The first convergence lenses 122 are disposed on both sides of the virtual plane O. The first convergence lenses 122 on both side of the virtual plane O is a plane-convex lens with its optical axis transpiercing the first light reception elements 110. The first convergence lens 122 is disposed between the second collimator lens 53 and the first light reception element 110. The optical axis of the first convergence lens 122 substantially has an angle of 45 degrees against the outer surface 9 of the windshield 4. The first convergence lens 122 receives the light in the first light path L1 that has the first collimator lens 52, the first reflector 54, the outer surface 9 of the windshield 4, and the prism 56 on one side of the virtual plane. Then, the first convergence lens 122 redirects the light toward the first light reception element 110. An oval area D1 shown in an illustration in FIG. 16 is a detection area on the outer surface 9 on the windshield 4. The light redirected in the detection area D1 can be received by the first light reception element 110. The amount r1 of the light received by the first light reception element 110 decreases when the detection area D1 is covered by moisture, e.g., raindrops. That is, in FIG. 4, the area D1 is the area that is used for raindrop detection in a rectangular projection area S of the raindrop detection device 100 on the windshield 4.

Two second convergence lenses 123 are disposed on the substrate 40, that is, one on each side relative to the virtual plane O. Two second reflectors 126 are also disposed on both sides of the virtual plane O. That is, each of the both sides of the virtual plane O has one second reflector 126. The second reflector 126 is substantially perpendicular to the outer surface 9 of the windshield 4 and to the panel surface 42 of the substrate 40. The second reflector 126 is positioned on the second end 45 side of the substrate 40 relative to the first light reception element 110. The second reflector 126 receives the light in the second light path L2 that passes through the second collimator lens 53 to be redirected by the outer surface 9 of the windshield 4 toward the prism 56. Then, the light from the prism 56 is redirected by the second reflector 126 toward the second convergence lens 123 on the same side relative to the virtual plane O.

The second convergence lens 123 is a plane-convex lens with its optical axis reflectively transpiercing the first light reception element 110 and the second reflector 126 on the same side relative to the virtual plane O. The second convergence lens 123 is positioned between the first light reception element 110 and the second reflector 126. The optical axis of the second convergence lens 123 has an angle of substantially 45 degrees against the outer surface 9 of the windshield 4, and also has an angle of substantially 90 degrees against the optical axis of the first convergence lens 122 on the same side relative to the virtual plane O. The second convergence lens 123 receives the light in the second light path L2 from the second reflector 126 on the same side relative to the virtual plane O, and redirects the light toward the first light reception element 110 on the same side relative to the virtual plane O. An oval area D2 shown in an illustration in FIG. 16 is a detection area on the outer surface 9 on the windshield 4. The light redirected in the area D2 can be received by the first light reception element 110. The area D2 is positioned outside of the detection area D1 in the present embodiment. The amount r1 of the light received by the first light reception element 110 decreases when the area D2 is covered by moisture, e.g., raindrops. That is, in FIG. 4, the area D2 is the area that is used as a raindrop detection area D2 by using the light in the light path L2.

The initial rain detection and the regular rain detection in the present embodiment are described with reference to flowcharts in FIGS. 17 and 18.

Figure 17:
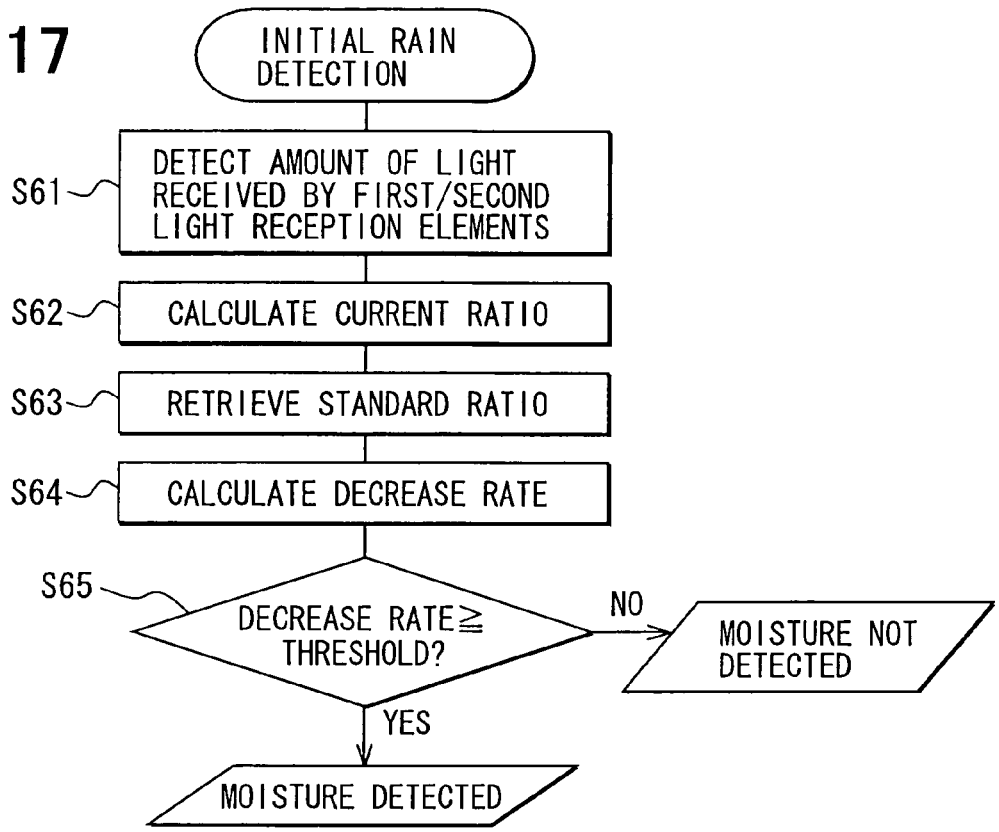
FIG. 17 shows a flowchart of wiper control process in an initial raindrop detection step in the fifth embodiment.

The initial rain detection in the fifth embodiment is shown as a flowchart in FIG. 17. In step S61, each of the two first light emitting elements 24 are used to emit the light in order, and the amounts r1, r2 of the light received by the first and second light reception elements 110 and 28 are detected. The light emission control circuit 22 and each of the detector/amplifier circuits 29 to 31 are respectively controlled by the control signals for setting the total emission amount of the light and the gain of the detection signals. The detection signals from the light reception elements 110 and 28 are processed by the detector/amplifier circuits 29 to 31, and are interpreted as the amounts of the received light r1, r1, r2 by the first and second light reception elements 110,110 and 28. Then, the amounts r1, r1, and r2 are stored in the RAM 36.

In steps S62 and S63, the ratio of the amount r2 of the received light by the second light reception element 28 and the amount of r1+r1 of the received light by the two first light reception element 110 is calculated in the same manner as the first embodiment. That is, in step S62, the current ratio Cr is calculated by retrieving, from the RAM 36, the amounts of light r1, r1, r2 respectively received by the two first light reception elements 110 and the second light reception element 28. In step S63, the standard ratio Cm that represents dry condition of the windshield 4 is retrieved from the ROM 35.

In steps S64 and S65, the same process in steps S14 and S15 in the first embodiment are executed.

Figure 18:
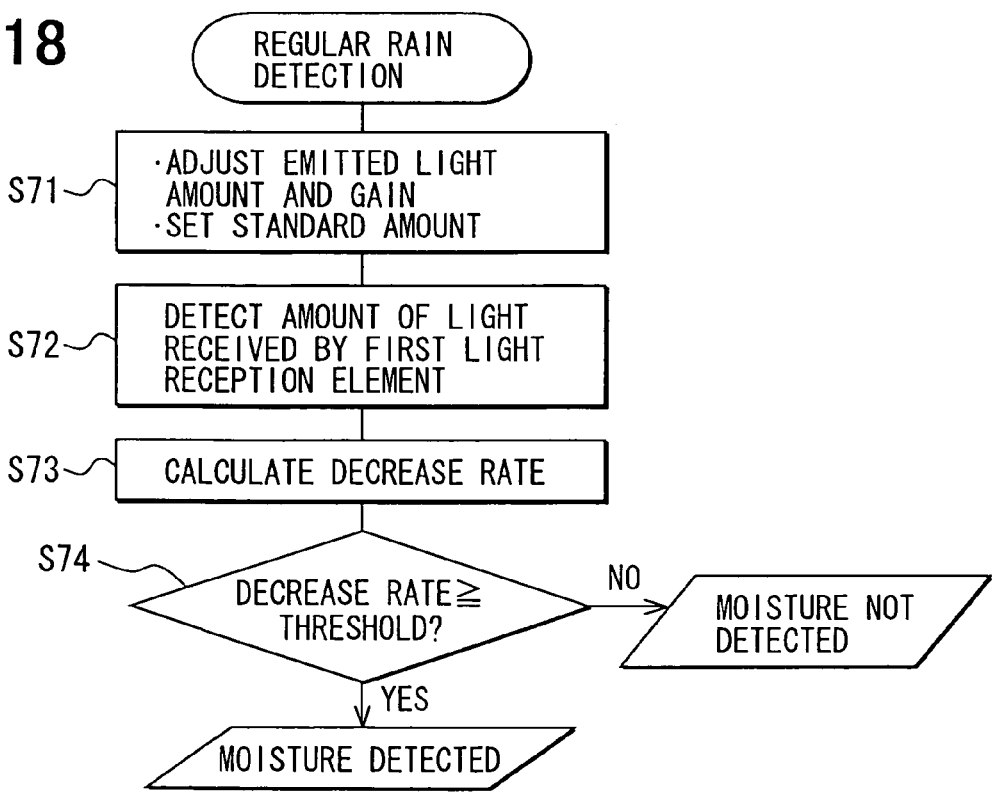
FIG. 18 shows a flowchart of wiper control process in a regular raindrop detection step in the first embodiment.

The regular rain detection in the fifth embodiment is shown as a flowchart in FIG. 18. In step S71, the total mount of emitted light from the light emitting elements 24 and the gain of the detector/amplifier circuits 29, 30 are adjusted by controlling the light emission control circuit 22 and the detector/amplifier circuits 29, 30. Step S71 is executed at the same timing as step S21 in the initial rain detection in the first embodiment. That is, step S71 is executed when there is no moisture on the windshield 4 immediately after the sweep of the wiper 5. In this manner, the amounts of received light r1, r1 by the first light reception elements 110 are defined as the standard amounts rb1, rb1.

In step S72, each the light emitting elements 110 are lit at a predetermined interval for measuring the amount of received light r1, r1. received by the two first light reception element 110. The total amount of emitted light from the light emitting element 24 and the gain of the detector/amplifier circuits 29, 30 are controlled to be the values that are defined in step S71. The amounts r1, r1 of light received by the light reception elements 26, 27 are processed by the detector/amplifier circuits 29, 30 in this step to be stored in the RAM 36.

In step S73, the ratio of the amount r1+r2 and the amount rb1+rb1 is calculated as the decrease rate F. In this step, the decrease rate F is calculated as a percentage.

In step S74, step S24 in the regular rain detection of the first embodiment is executed.

The fifth embodiment of the present invention determines whether there is moisture on the windshield 4 by calculating the ratio of the amount of light received by the first light reception element 110 against the amount of light received by the second light reception element 28. In this manner, temperature dependent factor is removed from the calculated ratio. Therefore, moisture on the windshield 4 can accurately be detected immediately after the wiper switch 12 is put in the "auto" position. Further, the standard ratio for use as detection criteria can be determined easily by collecting small amount of data. Furthermore, the simplified process for the regular rain detection decreases the process time of the detection. Furthermore, the detection area in the projection area of the raindrop detection device 100 is highly efficiently arranged in terms of space utilization. Furthermore, the detection areas D1 and D2 are covered by only one light reception element 110, thereby enabling to have a reduced number of components and a reduced cost of production.

Furthermore, integrated body of the optical device 120 having the prism 56 and lenses 52, 53, 122, 123 combined therein contributes to the ease of assembling.

Furthermore, the arrangement of the reflectors 54, 126 and the optical device 120 contributes to compactness of the body of the raindrop detection device 100. In this manner, a driver of the vehicle can have an increased area of view through the windshield 4.

Although the present invention has been fully described in connection with the preferred embodiments thereof with reference to the accompanying drawings, it is to be noted that various changes and modifications will become apparent to those skilled in the art.

Figure 19:
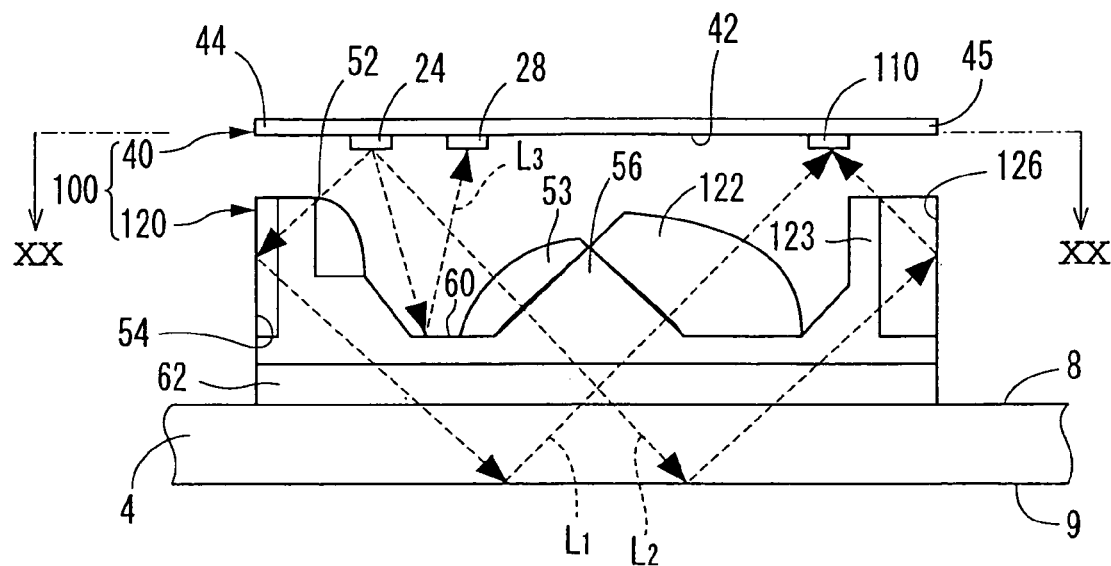
FIG. 19 shows a side view of modification of the raindrop detection system in the fifth embodiment.
Figure 20:
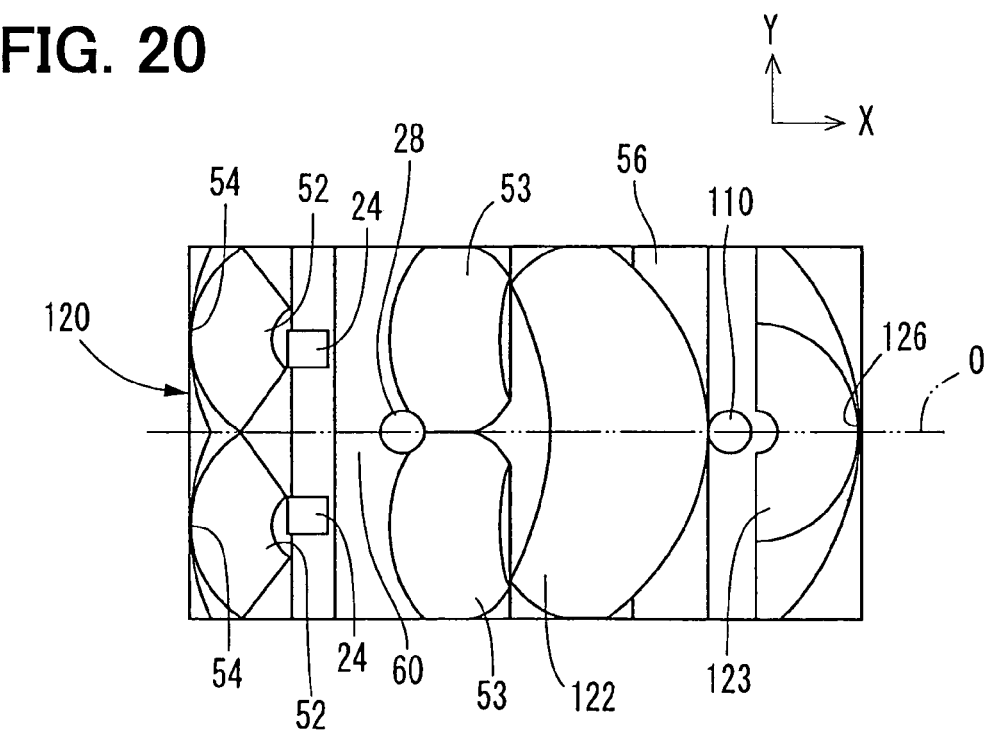
FIG. 20 shows a cross sectional view of the raindrop detection system along XX-XX line of the raindrop detection system in FIG. 19.

For example, the raindrop detection device 100 may use only one first light reception element 110 instead of two. Further, the first and the second convergence lenses 122, 123 may respectively be a single plane-convex lens having a round shape over the entire width in Y direction of the substrate 40 instead of two divided form of lenses by the virtual plane O. Furthermore, the second reflector 126 may have a single reflective surface instead of two surfaces divided by the virtual plane O. In this manner, a modification of the fifth embodiment can have the same effect as the fifth embodiment by replacing two amounts r1, r1 of light with one amount r1. The modification of the fifth embodiment is shown in FIGS. 19 and 20.

Furthermore, in the fifth embodiment, the regular rain detection in the fifth embodiment may be replaced with the initial rain detection as described in the second embodiment, or the regular rain detection in the third embodiment may be replaced with the regular rain detection in the fifth embodiment.

Furthermore, the initial rain detection in the fifth embodiment may be replaced with the initial rain detection as described in the second embodiment. In this case, the change rate Δ represents sum of the two amounts r1, r1.

Furthermore, at least one of the reflective surface 60, the first reflector 54, the second reflector 126 may be separately formed from the optical devices 50 or 120 in the embodiments described above.

Furthermore, the light reception element 28 may be disposed at the position of the reflective surface 60 for receiving the light in the third light path L3 directly from the light emitting element 24.

Such changes and modifications are to be understood as being within the scope of the present invention as defined by the appended claims.

What is claimed is:

1. A sensor device for detecting wetting on a windshield comprising:
    a control unit;
    a light emission element for emitting a light;
    a first light reception element for receiving the light in a first light path that includes reflective redirection by the windshield;
    a second light reception element for receiving the light in a second light path that does not include redirection by the windshield; and
    an optical device comprising a transparent portion adapted to transmit light therethrough and intersecting said first light path so that the first light path passes therethrough toward the windshield, the optical device further comprising a reflective surface for redirecting the light from the light emission element to the second light reception element without redirection by or passing into the windshield, the reflective surface being spaced from so as not to intersect the first light path;
    wherein a ratio of the amount of the received light by the first light reception element and the amount of the received light by the second light reception element is used by the control unit to determine the wetting on the windshield.

2. The sensor device according to claim 1,
    wherein the optical device is disposed between the light emission element and the windshield.

3. The sensor device according to claim 1,
    wherein an operation signal for automatically operating a wiper system is generated based on the ratio of the received light by the first light reception element and the received light by the second light reception element.

4. A sensor device for detecting a wetting on a windshield comprising:
    a control unit;
    a light emission element for emitting a light; and
    a first light reception element and a second light reception element for respectively receiving the light emitted by the light emission element,
    wherein the first light reception element receives a light path that includes redirection by the windshield,
    the second light reception element receives the light path that does not includes redirection by the windshield,
    the control unit controls an amount of emission of the light by the light emission element in the light paths to both of the first and second light reception elements, and
    a first ratio of the difference between two amounts of the received light by the first light reception element to the difference between two amounts of emitted light from the light emission element is compared by the control unit with a second ratio of the difference between two amounts of the received light by the second light reception element to the difference between two amounts of emitted light from the light emission element, for determining wetting on the windshield when the amount of emission of the light by the light emission element is changed by the control unit.

5. The sensor device according to claim 4,
    wherein determination of wetting on the windshield is conducted at least once upon receiving a determination instruction.

6. The sensor device according to claim 4,
    wherein a comparison result of the first ratio with the second ratio is stored in a memory.

7. The sensor device according to claim 4, further comprising:
    a reflective surface for redirecting the light from the light emission element to the second light reception element.

8. The sensor device according to claim 7, further comprising an optical device for passing the light in the first light path to the windshield,
wherein the optical device includes the reflective surface.

9. The sensor device according to claim 8, further comprising a substrate that is disposed in a position substantially parallel to the windshield for including the light emission element, the first light reception element and the second light reception element,
wherein the reflective surface is positioned between the substrate and the windshield.

10. A wiper controller for automatically controlling a wiper system comprising:
a driving mechanism for actuating the wiper system; and
a sensor device for detecting wetting on a windshield,
wherein the sensor device includes a control unit, light emission element for emitting a light, a first light reception element for receiving the light in a first light path that includes reflective redirection by the windshield, a second light reception element for receiving the light in a second light path that does not include reflective redirection by the windshield, and an optical device comprising a transparent portion adapted to transmit light therethrough and intersecting said first light path so that the first light path passes therethrough toward the windshield, the optical device further comprising a reflective surface for redirecting a light from the light emission element to the second light reception element without redirection by or passing into the windshield, wherein the reflective surface is spaced from so as not to intersect the first light path, and the sensor device determines a ratio of the amount of the received light by the first light reception element and the amount of the received light by the second light reception element by using the control unit.

11. A wiper controller for automatically controlling a wiper system comprising:
a driving mechanism for actuating the wiper system; and
a sensor device for detecting wetting on a windshield, wherein the sensor device includes a control unit; a light emission element for emitting a light, a first light reception element for receiving the light in a first light path that includes reflective redirection by the windshield, and a second light reception element for receiving the light in a second light path that does not include reflective redirection by the windshield, the control unit controls an amount of emission of the light by the light emission element in the light paths to both of the first and second light reception elements, and the sensor device determines a ratio of the amount of the received light by the first light reception element and the amount of the received light by the second light reception element by using the control unit,
wherein a first ratio of the difference between two amounts of the received light by the first light reception element to the difference between two amounts of emitted light from the light emission element is compared by the control unit with a second ratio of the difference between two amounts of the received light by the second light reception element to the difference between two amounts of emitted light from the light emission element, for determining wetting on the windshield when the amount of emission of the light by the light emission element is changed by the control unit.

* * * * *